(12) United States Patent
Hurlin et al.

(10) Patent No.: US 10,458,967 B2
(45) Date of Patent: Oct. 29, 2019

(54) METHOD AND APPARATUS FOR CREATING AN OPENING IN THE CALCIFIED SHELL IN THE REGION OF THE BLUNT END OF AN INCUBATED BIRD EGG WITH EMBRYO AND FOR DETERMINING THE SEX THEREOF

(71) Applicant: AGRI Advanced Technologies GmbH, Visbek (DE)

(72) Inventors: Jörg Hurlin, Dötlingen (DE); Sven Meissner, Brandersbidorf (DE); Björn Fischer, Limbach-Oberfrohna (DE)

(73) Assignee: AGRI ADVANCED TECHNOLOGIES GMBH, Visbek (DE)

( * ) Notice: Subject to any disclaimer, the term of this patent is extended or adjusted under 35 U.S.C. 154(b) by 0 days.

(21) Appl. No.: 15/742,767

(22) PCT Filed: Jul. 29, 2016

(86) PCT No.: PCT/EP2016/068243
§ 371 (c)(1),
(2) Date: Jan. 8, 2018

(87) PCT Pub. No.: WO2017/017277
PCT Pub. Date: Feb. 2, 2017

(65) Prior Publication Data
US 2018/0196024 A1 Jul. 12, 2018

(30) Foreign Application Priority Data
Jul. 29, 2015 (EP) .................................... 15178951

(51) Int. Cl.
*G01N 33/08* (2006.01)
*A01K 45/00* (2006.01)
(Continued)

(52) U.S. Cl.
CPC .......... *G01N 33/085* (2013.01); *A01K 43/00* (2013.01); *A01K 45/005* (2013.01);
(Continued)

(58) Field of Classification Search
CPC .... A01K 43/00; A01K 45/005; A01K 45/007; B07C 5/3416; B07C 3/04; G01N 33/085
(Continued)

(56) References Cited

U.S. PATENT DOCUMENTS 1,740,661 A 12/1929 Mauer
5,017,003 A * 5/1991 Keromnes ............ G01N 33/085
209/510
(Continued)

FOREIGN PATENT DOCUMENTS

DE        69905493 T2    12/2003
DE    102007013107 A1    9/2008
(Continued)

OTHER PUBLICATIONS

International Search Report from International Patent Application No. PCT/EP2016/068243, dated Oct. 10, 2016, 3 pages.
(Continued)

*Primary Examiner* — Terrell H Matthews
(74) *Attorney, Agent, or Firm* — Westman, Champlin & Koehler, P.A.

(57) ABSTRACT

According to the present invention, a method and an apparatus are provided for creating an opening in the calcified shell of an incubated bird egg containing an embryo, in the region of the blunt end of the incubated bird egg. Within the region of the blunt end there is an outer membrane and an inner membrane with an air cell located therebetween. The apparatus comprises a holder on which the incubated bird eggs are stored with their pointed ends facing downwards, wherein the embryo adjoins the inner membrane, a first
(Continued)

detection device configured to detect the position and geometry of the air cell, and an opening device configured to create an opening in the calcified shell at the blunt end of the incubated bird egg above the taut inner membrane. Due to the open calcified shell, the sex of the embryo may be determined in a reliable way.

18 Claims, 6 Drawing Sheets (51) Int. Cl.
    *A01K 43/00* (2006.01)
    *A01K 67/02* (2006.01)
    *G01N 21/65* (2006.01)
(52) U.S. Cl.
    CPC ............ *A01K 45/007* (2013.01); *A01K 67/02* (2013.01); *G01N 21/65* (2013.01)
(58) Field of Classification Search
    USPC .................................................. 209/510, 511
    See application file for complete search history.

(56) References Cited

U.S. PATENT DOCUMENTS

| | | | |
|---|---|---|---|
| 5,745,228 A * | 4/1998 | Hebrank | G01N 33/085 356/53 |
| 6,244,214 B1 | 6/2001 | Hebrank | |
| 2007/0024843 A1 * | 2/2007 | Hebrank | G01N 33/08 356/53 |
| 2007/0137577 A1 | 6/2007 | Wolfe et al. | |
| 2008/0149033 A1 * | 6/2008 | Hebrank | G01N 33/085 119/6.8 |
| 2008/0289578 A1 * | 11/2008 | Rybarczyk, Jr. | G01N 33/08 119/6.8 |
| 2011/0141455 A1 * | 6/2011 | Adjanohoun | G01N 33/085 356/55 |
| 2015/0136030 A1 | 5/2015 | Meissner et al. | |
| 2015/0138535 A1 * | 5/2015 | Walukas | G01N 33/085 356/51 |
| 2015/0260704 A1 | 9/2015 | Bruins et al. | |

FOREIGN PATENT DOCUMENTS

| | | |
|---|---|---|
| FR | 2912216 A1 | 8/2008 |
| WO | 2011088825 A1 | 7/2011 |
| WO | 2014021715 A2 | 2/2014 |

OTHER PUBLICATIONS

European Search Report from European Patent Application No. EP 15178951, dated Jan. 25, 2016, 8 pages.

International Preliminary Report on Patentability, including transmittal and Written Opinion, for International Application No. PCT/EP2016/068243, dated Feb. 8, 2018, 22 pages.

* cited by examiner

METHOD AND APPARATUS FOR CREATING AN OPENING IN THE CALCIFIED SHELL IN THE REGION OF THE BLUNT END OF AN INCUBATED BIRD EGG WITH EMBRYO AND FOR DETERMINING THE SEX THEREOF

CROSS-REFERENCE TO RELATED APPLICATION

This Application is a Section 371 National Stage Application of International Application No. PCT/EP2016/068243, filed Jul. 29, 2016, and published as WO 2017/017277 A1 on Feb. 2, 2017, in English, the contents of which are hereby incorporated by reference in their entirety.

The present invention relates to a method and an apparatus for creating an opening in the calcified shell in the region of the blunt end of an incubated bird egg containing an embryo. Within the region of the blunt end there is an outer membrane and an inner membrane with an air cell located therebetween, and the embryo adjoins the inner membrane at the hatching egg stored with its pointed end facing downwards.

The present invention further relates to a method and an apparatus for determining the sex of such embryos using optical data collected by irradiating the embryo through the open calcified shell.

In industrial poultry farming, hatching eggs of laying hen lines or broiler lines are put into so-called brooding trays at the beginning of the hatching process, wherein the eggs are placed in such a way that the blunt ends of the eggs and thus also the air cells within the eggs face upwards. Accordingly, the somewhat more pointed ends of the oval eggs face downwards. Subsequently, the brooding trays are initially inserted into a setter trolley or in tray shelves into the incubator. After a prescribed pre-hatching period, the hatching eggs are then relocated onto so-called hatching trays in order for the chicks to hatch.

Due to strong specializing in the field of chicken breeding (hybridization), the sexing of developing chicks is of extraordinary importance. At present, the sexing takes place manually and/or visually by means of cloaca morphology, the color of the feathers, or the shape of the feathers of certain feather regions immediately after hatching. The identified chicks are separated and brought to the respective breeding establishments or production plants. Particularly, male chicks of the laying hen lines are required for breeding only in small numbers (parents/grandparents) and/or are not suitable for grow-out due to their genetics and are therefore sorted out and killed immediately after hatching (end product).

Killing male day-old chicks by default has increasingly been causing ethical and legal concerns according to the German Animal Welfare Act. To date, however, practicable alternatives have not been available.

In conventional apparatuses for sexing incubated bird eggs, e.g., in WO 2011/088825 A1 or DE 10 2007 013 107 A1, a hole is formed in the calcified shell outside of the region of the air cell by opening both membranes during working on the calcified shell, wherein a strong impact on the hatching egg is accepted, and harm often arises so that oftentimes no further development of the embryo is possible after sexing, thus considerably reducing hatchability.

It is thus an object of the present invention to provide a method and an apparatus for creating an opening in the calcified shell in the region of the blunt end of an incubated bird egg with embryo, said method and apparatus being suitably configured such that the opening in the calcified shell is formed as an open access to the air cell without defectively impacting the inner membrane of the calcified shell in order to ensure further development of the embryo. It is another object of the present invention to provide a method and an apparatus for determining the sex of an avian embryo with which the risk of damaging the embryo is reduced or avoided.

These objects are achieved by the features of the independent claims. The dependent claims relate to further aspects of the present invention.

The present invention allows opening incubated bird eggs as carefully as possible without thereby damaging the inner membrane. With the help of the opening it is possible to determine the sex of the embryo non-invasively, e.g., with the help of optical, biological, or chemical methods, for instance, spectroscopic methods such as Raman spectroscopy and/or fluorescence spectroscopy. According to the invention, the bird eggs may be closed again after the sex has been determined. Thus, further development of the embryo is ensured.

An essential advantage is that by preserving the inner membrane, the interior of the egg, i.e. the developing embryo, remains mostly unaffected and higher hatchability rates can be achieved in comparison to other opening methods.

According to an aspect of the present invention, a method for creating an opening in the calcified shell in the region of the blunt end of an incubated bird egg with embryo is provided, wherein within the region of the blunt end there is an outer membrane and an inner membrane with an air cell located therebetween. The method comprises the following steps:
a) storing the incubated bird eggs with their pointed ends facing downwards, wherein the embryo adjoins the inner membrane;
b) candling the incubated bird egg and detecting the light transmitted through the incubated egg for detecting the position and the geometry of the air cell at the blunt end of the incubated bird egg; and
c) subsequently creating an opening in the calcified shell at the blunt end of the incubated bird egg above the taut inner membrane to the air cell in order to obtain an access to the air cell.

The method may further comprise a step for detecting the position and geometry of the incubated bird egg, wherein the incubated bird egg is preferably placed on a predetermined brooding tray.

The step for detecting the position and geometry of the air cell may comprise a step for determining a two-dimensional projection of the air cell with a central point m from the detected light transmitted through the incubated egg, wherein the two-dimensional projection of the air cell comprises an essentially elliptic, optionally circular, shape with the point of intersection of intersecting major and minor axes A, B of the ellipse as a central point m.

The central point m may be used as the center for creating the opening, wherein the opening is preferably circular and has a radius R that at the most corresponds to half the minor axis of the ellipse.

According to the present invention, the creation of the opening may comprise a step for creating a predetermined breaking point in the calcified shell, wherein the creation of the opening may comprise a step for removing the region of the calcified shell defined by the predetermined breaking point.

The method may further comprise a further step for candling the incubated bird egg after creating the opening, and a step for detecting the light transmitted through the incubated bird egg, wherein light in the spectral range between 500 nm and 600 nm is preferably used in order to capture the embryo-specific target structures.

Prior to detecting the light transmitted through the incubated bird egg, the method may comprise a step for determining the distance a of the inner membrane starting from the vertex of the egg's blunt end, and a step for focusing the inner membrane using the distance a.

The method may further comprise a step for detecting the position of the embryo using the detected light transmitted through the incubated bird egg.

Furthermore, the method may comprise a step for determining the sex of the embryo, wherein the step for determining the sex of the embryo may comprise a step for measuring optical data, preferably using absorption spectroscopy, particularly Raman spectroscopy or fluorescence spectroscopy, or using chemical or biological data.

After the creation of the opening, the method may further comprise a step for closing the opening, preferably with a semipermeable membrane composed of a biocompatible material.

The method may further comprise a step for disinfecting at least the blunt end of the incubated bird egg.

The method may also comprise a step for conveying the incubated bird eggs and a step for returning the incubated bird eggs.

According to another aspect of the present invention, an apparatus for creating an opening in the calcified shell of an incubated bird egg with embryo in the region of the blunt end of the incubated bird egg is provided, wherein within the region of the blunt end there is an outer membrane and an inner membrane with an air cell located therebetween, wherein the apparatus is preferably adapted to carry out the above-described method. Accordingly, the apparatus comprises a holder, preferably a brooding tray, which is configured to store the incubated bird egg with its pointed end facing downwards, wherein the embryo adjoins the inner membrane. The apparatus further comprises a first detection device configured to detect the position and geometry of the air cell, wherein the first detection device comprises a first candling device configured to transmit light through the incubated bird egg, and a first detector configured to record the light transmitted through the incubated bird egg. The apparatus further comprises an opening device configured to create an opening in the calcified shell at the blunt end of the incubated bird egg above the taut inner membrane to the air cell so as to obtain an access to the air cell.

The first candling device may be arranged below the incubated bird egg, and the first detector may be arranged above the incubated bird egg and opposite the first candling device.

The first detection device may further be configured to detect the position and geometry of the incubated bird egg stored with its pointed end facing downwards, wherein the apparatus further preferably comprises a brooding tray on which the incubated bird egg is stored.

The first detection device may be a sensor or a sensor array and may preferably comprise a distance sensor or a triangulation sensor.

The apparatus may further comprise an analysis and control unit configured to determine a two-dimensional projection of the air cell with a central point m by using the detected light, wherein said two-dimensional projection of the air cell comprises an essentially elliptic, optionally circular, shape with the point of intersection of intersecting major and minor axes A, B of the ellipse as a central point m.

The analysis and control unit may further be configured to determine a substantially circular opening, wherein the center of the opening corresponds to the central point m and preferably comprises a radius R that corresponds to at the most half the minor axis of the ellipse.

The opening device may comprise a working device configured to create a predetermined breaking point in the form of the opening, wherein the working device preferably is a laser-optical device configured to perforate the calcified shell with a laser beam.

The opening device may further comprise a removal device configured to remove the region defined by the predetermined breaking point.

The apparatus may also comprise a second candling device arranged below the incubated bird egg and configured to send light through the incubated bird egg, wherein light in the spectral range between 500 nm and 600 nm is preferably used.

The apparatus may further comprise a second detector arranged above the incubated bird egg and opposite the second candling device, wherein the second detector is configured to record the light transmitted through the incubated bird egg.

The analysis and control unit may further be configured to detect the position of the embryo by using the light transmitted through the incubated bird egg and recorded by the second detector.

The apparatus may further comprise a sex determination unit configured to determine the sex of the embryo, wherein the sex determination unit may be an optical measurement unit, preferably an absorption spectroscopy unit, particularly a Raman spectroscopy unit or a fluorescence spectroscopy unit, or a chemical measurement unit or a biological measurement unit.

The apparatus may further comprise a closing device configured to close the opening, preferably using a semipermeable membrane composed of a biocompatible material.

The apparatus may also comprise a disinfection device configured to disinfect at least the blunt end of the incubated bird egg.

The apparatus may further comprise a transportation device configured to transport the incubated bird egg in a transporting direction, wherein the transportation device may further comprise a conveying device configured to convey the incubated bird egg to the apparatus, and wherein the transportation device may further comprise a returning device configured to return the incubated bird egg from the apparatus.

According to the present invention, a method is provided for creating an opening in the calcified shell in the region of the blunt end of an incubated bird egg with embryo stored with its pointed end facing downwards. Within the region of the blunt end there is an outer membrane and an inner membrane with an air cell located therebetween, wherein the embryo adjoins the inner membrane. The hatching eggs to be investigated may rest in a predetermined enclosure. Furthermore, the hatching egg stored with its pointed end facing downwards may be measured, wherein the position and dimensions of the air cell within the range of the blunt end and the location of the embryo below the inner membrane shielding the embryo from the air cell may be detected. A two-dimensional projection of the hatching egg with a center M and a two-dimensional projection of the air cell with a central point m overlaying therewith may be made, wherein the two-dimensional projection of the air cell comprises, e.g., an elliptic shape with the point of intersection m of intersecting major and minor axes A, B of the ellipse. The central point of a projection of the breaking point to be assigned to the purposed opening may be assigned to the point of intersection m of the major and minor axes A, B of the ellipse. A calcified shell lid corresponding to the two-dimensional projection of the breaking point may be lifted and removed from the calcified shell. An opening and thus also an access to the detected air cell may in this way be obtained in the calcified shell and in the outer membrane adhering to the calcified shell.

The breaking point projection for the predetermined breaking point may illustrate a circular projection, wherein the radius R of the circular projection is smaller than half the length A/2 of the minor axis A of the ellipse with R<A/2.

Before the hatching eggs are measured, the hatching eggs in the enclosure are disinfected, preferably in the region of their blunt ends.

Preferably, one or more of the following steps may subsequently be carried out using an analysis and control unit: detecting the positions and geometries of the hatching eggs stored with their pointed ends facing downwards and resting on a predetermined brooding tray; detecting the geometry of the air cell at the blunt end of the hatching egg; detecting and digitalizing the geometric data of the volume of the air cell; determining a two-dimensional outline in the form of an area projected onto a surface in a digitalized camera image from the volume projection of the air cell in the shape of an ellipse; calculating the point of intersection m of the major and minor axes A, B of the ellipse from the digitalized camera image; calculating the projection of the breaking point and the corresponding ditch-like predetermined breaking point with respect to the point of intersection m of the ellipse; as well as overlaying the projection of the breaking point with the projection of the air cell; creating an opening in the calcified shell in the projection of the breaking point located centrically to the point of intersection m of the ellipse via the predetermined breaking point above the taut inner membrane by means of a working device; and removing the separated part of the calcified shell as a lid according to the defined breaking point and creating the opening.

The distance a of the inner membrane may be determined from the vertex of the egg of the blunt end, wherein the distance a is used for focusing the color camera on a target structure in the region of the inner membrane.

After the calcified shell has been opened, the hatching egg may be candled again for a second time, and a picture of the detected region of the inner membrane of the air cell may be taken by means of the color camera for determining the target structure for collecting measurement data of the target structure with respect to the egg and the embryo.

The egg-specific and embryo-specific measurement data of the target structure may be collected using absorption spectroscopy, e.g., Raman spectroscopy or fluorescence spectroscopy.

An adjusted contrasting of the embryo-specific target structures lying beneath the inner membrane may be set using a light source, preferably in the spectral range between 500 nm and 600 nm with the second candling device.

After the egg-specific and embryo-specific features have been collected and measured, the opening in the air cell may be closed by means of a locking element in the form of a semipermeable membrane.

At least one enclosure with hatching eggs in which the hatching eggs are held in a sorted manner may be assigned to the transportation device.

A marking may be chosen at an enclosure for the hatching eggs or at the transportation device as a determinable region of the opening if the positioning device installed in the region of the conveying device is oriented so as to determine the position of the enclosure and if the first positioning device is arranged above the enclosure.

The step of creating an opening in the calcified shell region constitutes a defined treatment of the hatching egg, wherein the initial positioning of the hatching egg is carried out by means of a sensor or a sensor array, and the final positioning of the hatching egg which is assigned to the creation of the opening and which corresponds to the associated setting position of the working device is carried out using the programmatic means saved in the analysis and control unit.

The working device may be positioned precisely at a predetermined and non-stationary position for creating the opening with respect to the calcified shell region of the hatching egg that is to be worked on with the help of the data received from a distance sensor or a triangulation sensor or a grazing light sensor, wherein the data are assigned to the respective hatching egg.

By means of the transportation device, the enclosure in the form of a tray for hatching eggs may be moved beneath the first detection device and the working device for creating the opening, wherein by means of the first detection device a 2D image section or a 3D image section of the top view of the hatching egg is captured with the data of said image section being transmitted via the electrical connecting lines to the analysis and control unit for further processing. In the analysis and control unit, the image data of the 2D image section can be processed together with the egg distance data from the distance sensor or the triangulation sensor by means of activated programmatic means, and the processed signals received may be forwarded to the working device in order to create a predetermined breaking point.

The opening of the calcified shell of the hatching egg in the region of the air cell created from the outside may also be created by means of mechanical, chemical, or water jet tools.

The following structural components may be part of the apparatus according to the present invention: a conveying device, a transportation device for transporting the enclosure, a positioning device for detecting the positions and the locations of the hatching eggs in the enclosure, a first detection device for determining the dimension of the egg, a second detection device with a first candling device and a color camera for determining the dimensions of the air cell, and a working device which creates a predetermined breaking point in the calcified shell calculated in an analysis and control unit along the ditch-like predetermined breaking point and identifies it as a lid to be lifted. Furthermore, the following structural components may be part of the apparatus: a device for lifting and removing the lid and for creating an opening in the air cell, a color camera with a second candling device for capturing and focusing the target structure to be investigated in the region of the inner membrane within the air cell, a unit for collecting measurement data with respect to the egg and the embryo of the target structure with a measuring probe in the beam path that is directed to the target structure, a closing device that closes the open air cell with a locking element, a returning device and an analysis and control unit in signaling communication, e.g., via connecting lines, with the aforementioned structural components and directing with an algorithm the creation of the opening to the air cell.

The unit for collecting measurement data with respect to the egg and the embryo of the target structure may be an absorption spectra collection unit, e.g., a Raman spectra collection unit or a fluorescence spectra collection unit.

The apparatus may further comprise a transportation device with the help of which at least one hatching egg is conveyed and returned within the apparatus, a first detection device for detecting a region relating to the hatching eggs and for converting the data of said region into electrical data, a second detection device for determining the dimensions of the air cell with the first candling device, a working device for creating a predetermined breaking point for creating an opening in the calcified shell, said working device receiving working signals from the analysis and control unit for working, a device for lifting the lid along the predetermined breaking point thus creating the opening in the air cell, a color camera for focusing on a target structure of the inner membrane using the second candling device, a unit for collecting measurement data with respect to the egg and the embryo of the target structure, a closing device, and an analysis and control unit.

The measurement data recorded in the unit for collecting measurement data with respect to the egg and the embryo of the target structure may, e.g., constitute optical measurement data, preferably measurement data from the absorption spectroscopy used such as, e.g., Raman spectroscopy or fluorescence spectroscopy, or chemical or biological measurement data.

A device for disinfecting at least the region of the blunt end may be arranged at least in front of the working device.

The deployed locking element may consist of a biocompatible material.

A sensor or a sensor array may be deployed as a first detection device to which optionally a distance sensor or a triangulation sensor is assigned.

At least one enclosure/tray/hatching tray with hatching eggs in which the hatching eggs are held in a sorted manner may be assigned to the transportation device.

A positioning device may be assigned to the standardized or predimensioned enclosures with constant distances $A_B$, $A_E$, $A_S$ of the bulges for receiving the eggs in order to determine the positioning areas of the sorted hatching eggs, said positioning device being geared only to the required determination of the enclosure so that the positioning areas of the hatching eggs may be determined from the constant distances $A_B$, $A_E$, $A_S$.

The positioning device may serve for the purpose of determining a region relating to the hatching eggs from the enclosure or a positioning area of at least one hatching egg in the enclosure, wherein the positioning device detects a predetermined marking of the enclosure, and wherein the positioning area of the respective hatching egg is determined in the analysis and control unit from the predetermined distances $A_B$, $A_E$, $A_S$ of the bulges for receiving the eggs of the enclosure with respect to each other and to the marking of the enclosure.

The apparatus may further comprise at least one sensor or a sensor array configured as a first detection device for capturing a 2D image section or a 3D image section in top view of the calcified shell region of at least one conveyed hatching egg, and optionally at least one distance sensor or a triangulation sensor, wherein the sensor collects the position data of the conveyed hatching egg. The apparatus may further comprise an analysis and control unit which collects and processes the egg position data and the position data, preferably the data of the predetermined breaking point, of the working device for creating the predetermined breaking point, wherein the working device for creating a predetermined breaking point in the calcified shell receives from the analysis and control unit the executive working signals that are necessary for working on the egg.

The working device for creating an opening in the predetermined breaking point may be a laser-optical device which perforates the calcified shell with its laser beam and forms a ditch-like predetermined breaking point.

The transportation device may be configured as a conveying device and as a returning device in a continuous form.

The sensor or the sensor array as well as the working device may be arranged above the transportation device and above the hatching eggs resting in the transported enclosure.

In principle, the whole arrangement of the aforementioned structural components may constitute an automated production line.

As per the method according to the invention, the following steps may preferably be carried out: transmitted light radiation and projection for exposing the position of the air cell in the incubated bird egg with embryo, creating an opening in the calcified shell, wherein the opening is projected centrally onto the surface of the inner membrane, and closing the open air cell by means of at least one semipermeable membrane in order to ensure the gas exchange of the air cell with the external air after the measurement recording, in particular the spectroscopic process, has been carried out, and maintaining sterility.

Since noncontact laser-optical procedures can ideally be incorporated in poultry industry processes, an apparatus based on a $CO_2$ laser, more specifically, an Nd:YAG laser or an Er:YAG laser, is preferably used for working on the calcified shell of hatching eggs. Other laser techniques may also be used.

The present invention is described in more detail by means of an exemplary embodiment with the help of the Figures.

In the following, the functionality of the apparatus according to the present invention and the method according to the present invention are explained in more detail with reference to FIG. 1 to FIG. 6.

Figure 1:
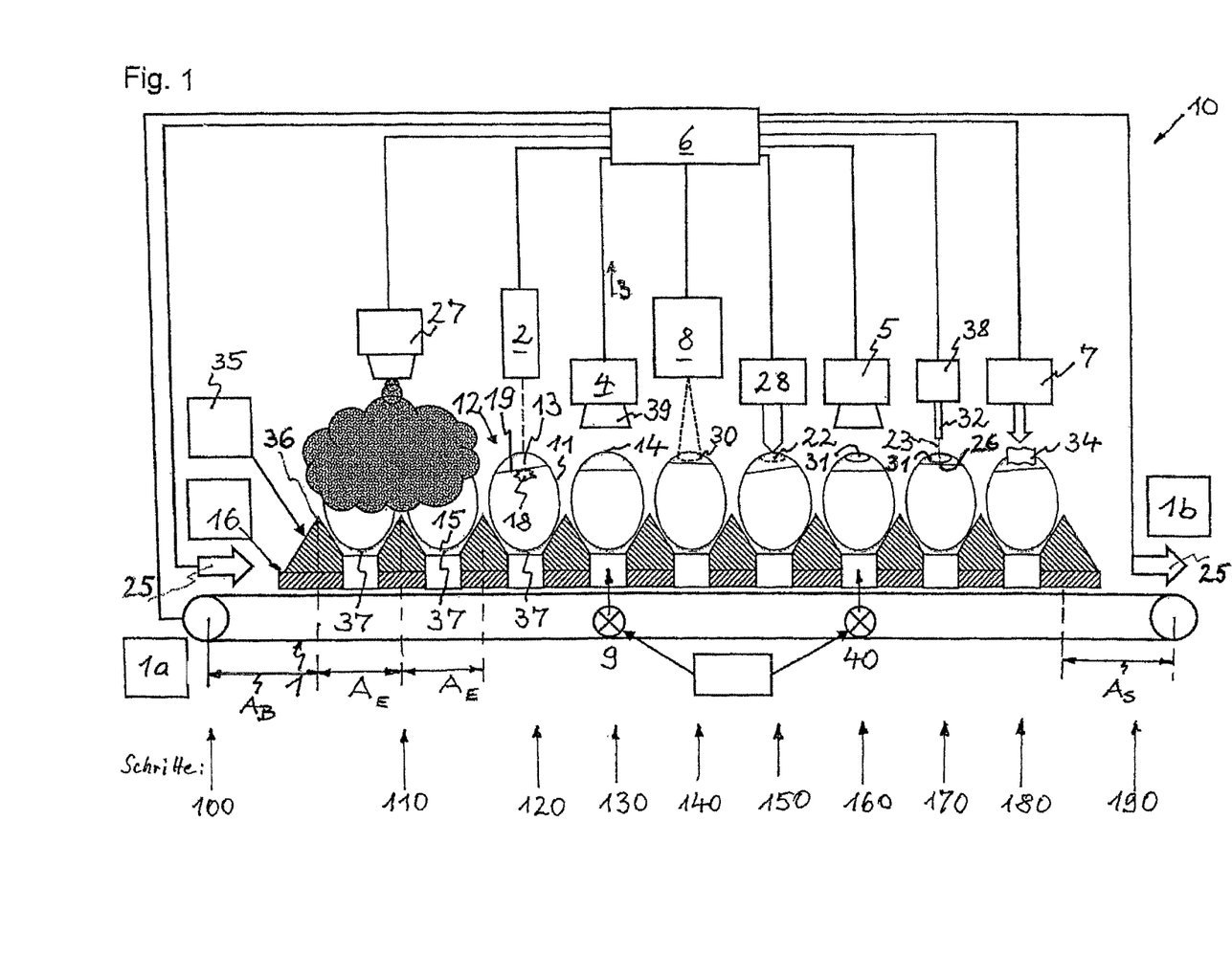
FIG. 1 a schematic illustration of an apparatus according to the invention for creating an opening in the calcified shell of an incubated bird egg containing an embryo in the region of the blunt end thereof with a plurality of structural components above an enclosure containing hatching eggs, particularly for creating an opening in the direction to the air cell in the region of the blunt end of an incubated bird egg with embryo, and for determining the sex of the embryo, FIG. 2 a schematic sectional view of bird eggs with avian embryos with a potential formation of the inner membrane, wherein the eggs stored on brooding trays are candled from below, starting from the pointed end, by light sources arranged below the brooding tray, preferably by means of white light, FIG. 3 a schematic illustration of a projection of the egg and the projection of the corresponding air cell, FIG. 4 a schematic illustration according to FIG. 3 with a circular opening determined to be located in the center of the air cell projection as a predetermined breaking point for creating the opening in the calcified shell in order to create an access to the air cell, FIG. 5 a schematic view of an egg dimensioned with the help of an optical distance meter for measuring the distance a of the inner membrane from the vertex of the egg of the blunt end for focusing on the target structure by means of collecting and detecting characteristic features of the target structure, and FIG. 6 a Raman spectrum that is measured at the intact inner membrane of the air cell in the region of the blunt end according to the present invention.

FIG. 1 shows an apparatus 10 for creating an opening 31 in the calcified shell 11 in the region of the blunt end 14 of an incubated bird egg 12 containing an embryo 18. Within the region of the blunt end 14 there is an outer membrane 20 and an inner membrane 19 with an air cell 13 located therebetween. The embryo 18 adjoins the inner membrane 19 of the hatching egg 12 stored with its pointed end 15 facing downwards. The hatching eggs 12 are held in a sorted manner in an enclosure 16. The exemplary embodiment according to FIG. 1 comprises a transportation device 1 to which the enclosure 16 is assigned in the form of a tray in which the hatching eggs 12 are sorted with their blunt ends 14 facing upwards, wherein the enclosure 16 is configured such that the hatching eggs 12 are stored at the positioning areas 37 at equal distances $A_E$, and a positioning device 35 which detects a marker 36 or a marking or an edge at the enclosure 16 from which the predetermined positioning areas 37 of the hatching eggs 12 are determined by means of predetermined distances A within the enclosure 16. The apparatus further comprises at least one detection device 2 which detects the dimensions (surface geometry) of the hatching egg 12, a detection device 4 for determining the dimensions of the air cell 13 with a candling device 9 and a color camera 39, a working device 8 for creating a predetermined breaking point 30 in the calcified shell 11, wherein after working on the calcified shell 11 the calcified shell 11 comprises ditch-like predetermined breaking points 30, and a device 28 for lifting and removing (removal device) the lid 22 defined by the predetermined breaking point 30, and creating an opening 31 in the air cell 13. Furthermore, the apparatus according to FIG. 1 comprises a color camera 5 with a second candling device 40 for detecting and focusing the structure 26 to be investigated in the region of the inner membrane 19 within the air cell 13, a Raman spectra recording unit 38 with a measuring probe 32 in the beam path 23 being directed to the structure 26, a closing device 7 with locking elements 34, and an analysis and control unit 6 that is connected with all structural components via a connecting line each.

In general, as is shown in FIG. 1, the enclosures/brooding tray 16 are, e.g., configured pallet-like such that the distances $A_E$ between the hatching eggs 12 themselves and the distances $A_B$ (beginning of the enclosure) and the distances $A_S$ (end of the enclosure) are standardized between the hatching eggs 12 and, e.g., an edge of the enclosure 16 and that the standardized values have already been or may already be saved and available in the analysis and control unit 6 so that they can be processed without signaling problems for setting the respective position of the opening device 8 for creating the opening 31 for calculating/determining the assigned calcified shell regions of the hatching eggs 12.

That is to say, a positioning device 35 may preferably be deployed for standardized or predimensioned brooding trays 16 with constant distances $A_B$, $A_E$, $A_S$ of the bulges for receiving the eggs in order to determine the positioning areas 37 of the sorted hatching eggs 12, said positioning device being geared only to the required detection of the brooding tray 16 so that the positioning areas 37 of the hatching eggs 12 may be determined from the constant distances $A_B$, $A_E$, $A_S$.

In addition to or inclusive of the detection device 2 in the form of a sensor or a sensor array, a distance sensor or a triangulation sensor may optionally be deployed. The sensors arranged in addition to the detection device 2 substantially serve for ensuring the accuracy during a continuous course of the process.

The region of the air cell 13 detected by the detection device 4 with the help of a camera 39 in combination with a first device 9 for candling the egg 12 with white light may be a 2D image section 3 in the form of a two-dimensional projection, or a 3D image section that is modified to be a two-dimensional projection.

The 2D image section 3 underlies the analysis and control unit 6 for processing, wherein in the analysis and control unit 6 the projection of the air cell 13 is assigned to the projection of the egg 12, and the projection of the air cell 13 is overlaid by a circular projection 21, wherein the circular projection 21 determines the dimensions of the entrance area of the opening 31.

According to the invention, the apparatus 10 contains, e.g., a conveying device 1a, a transportation device 1 for transporting the enclosure 16, a positioning device 35 for determining the locations of the hatching eggs 12 in the enclosure 16, and a detection device 2 for detecting the dimensions of the eggs. The apparatus 10 may further comprise a detection device 4 with a first candling device 9 and a color camera 39 for detecting the dimensions of the air cell 13, a working device 8 which creates a predetermined breaking point 30 in the calcified shell 11 along the predetermined breaking point 30 that was calculated in an analysis and control unit 6 and which identifies said predetermined breaking point 30 as a lid 22 to be lifted, a device 28 for lifting and removing the lid 22 and for creating an opening 31 in the air cell 13, and a color camera 5 with a second candling device 40 for detecting and focusing the structure 26 to be investigated in the region of the inner membrane 19 within the air cell 13. Furthermore, the apparatus 10 may comprise a Raman spectra recording unit 38 with a measuring probe 32 in the beam path 23 being directed to the target structure 26, a closing device 7 which closes the open air cell 13 with a locking element 34, a returning device 1b and an analysis and control unit 6 which is in signaling communication with all aforementioned structural components via connecting lines and which directs with an algorithm the creation of the opening 31 to the air cell 13.

A device 27 for disinfecting (disinfection device) at least the region of the blunt end 14 may be arranged at least in front of the working device 8.

A closing device 7 with locking material for closing the created opening 31 of the air cell 13 is arranged downstream of the working device 8.

The locking element 34 may consist of a biocompatible material.

A sensor or a sensor array to which optionally a distance sensor or a triangulation sensor is assigned may be used as a first detection device 2.

At least one enclosure/tray/hatching tray 16 with hatching eggs 12 in which the hatching eggs are held in a sorted manner is assigned to the transportation device 1, 1a, 1b.

According to FIG. 1, the positioning device 35 detects a predetermined marking 36 of the enclosure 16 and determines, with the help of the predetermined distances $A_B$, $A_E$, $A_S$ of the bulges for receiving the eggs of the enclosure 16, the positions of the eggs 12 to each other and determines in the analysis and control unit 6 the respective positioning area 37 of the respective hatching egg 12 with respect to the marking 36 of the enclosure 16.

The apparatus 10 may comprise at least one sensor 2 or a sensor array configured as a detection device 18a for capturing a 2D image section 3 or a 3D image section in top view of the calcified shell region of at least one conveyed hatching egg 12, and optionally at least one distance sensor or a triangulation sensor, wherein the sensor 2 detects the positioning data of the conveyed hatching egg 12, and an analysis and control unit 6 which collects and processes the data regarding the position of the egg as well as the positioning data of the working device 8 for creating an opening 31, wherein the working device 8 receives from the analysis and control unit the working signals to be executed that are necessary for processing in order to create the opening 31 in the calcified shell 11.

The transportation device 1 may be configured as a conveying device 1a and as a returning device 1b in a continuous form.

The sensor 2 or the sensor array as well as the working device 8 may be arranged, e.g., above the transportation device 1, 1a, 1b as well as above the hatching eggs 12 resting in the transported enclosure 16.

In FIG. 1, the working device 8 for creating the predetermined breaking point 30 may be a laser-optical device which creates a predetermined breaking point 30 in the calcified shell 11 by means of perforating the calcified shell 11 and a final breakthrough. The laser-optical device 8 may also be configured as a retraceable, movable device.

A device 28 for lifting the cut-free lid 22 is arranged thereafter.

This is followed by a color camera 5 of a second device 40 for candling the hatching egg 12 for a second time in order to determine the measuring location at the inner membrane 19.

A Raman measuring probe 32 absorbing a scattered radiation is assigned to the downstream Raman spectra recording unit 38, said Raman measuring probe 32 recording the Raman scattered radiation via the beam path 23.

With the help of the closing device 7 arranged thereafter, a locking element 34 is applied to the opening 31 for closing said opening 31.

In FIG. 1, the conveying device 1a and the returning device 1b are part of a consistent transportation device 1 comprising a predetermined running direction 25.

For positioning and releasing the opening process, programmatic means are saved in the analysis and control unit 6, said programmatic means completing the course of the process as per a predetermined algorithm, wherein the analysis and control unit 6 is in electrical communication with all structural components of the various devices.

The sensor or the sensor array as the detection device 2 for dimensioning the egg sends the 2D image section 3 of the captured top view of the hatching egg 12 to the analysis and control unit 6 via electrical connecting lines provided. The sensor 2 or the sensor array and the laser-optical opening device 8 are arranged above the transportation device 1 as well as above the hatching eggs 12 resting in the brooding tray/enclosure 16.

With the help of the detection device 4 for the air cell present in the form of a distance sensor or a triangulation sensor, the laser-optical working device 8 is positioned exactly above the hatching egg 12. For this purpose, the laser-optical opening device 8 receives positioning and working signals from the analysis and control unit 6 which, for instance, can be a PC.

Figure 4:
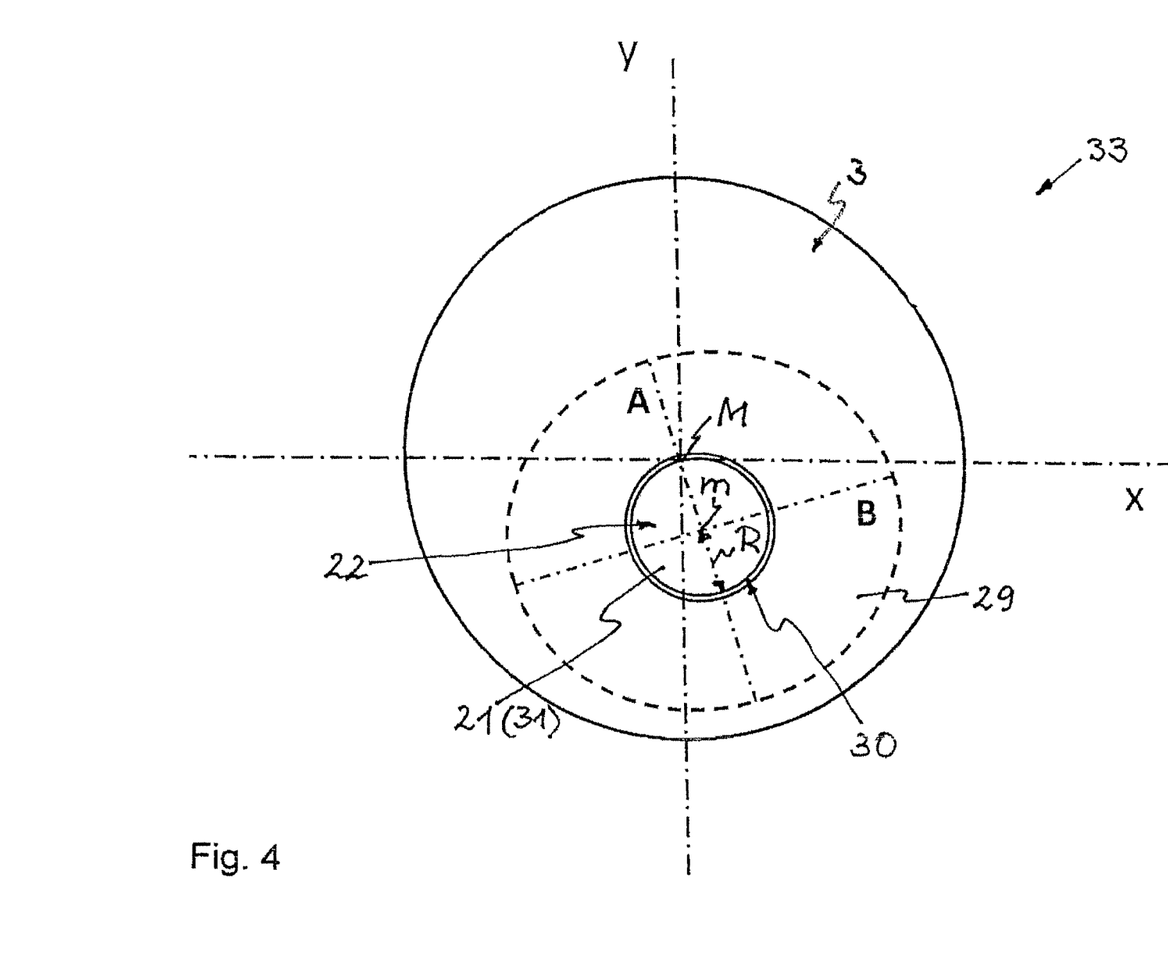

In general, the air cell 13 is located in the region of the blunt end 14. As shown in FIG. 4, a calcified shell lid 22 may be precisely removed by applying a contour corresponding to the predetermined breaking point 30.

According to FIG. 4, the opening created from the outside may comprise a guideway 30 in the form of the predetermined breaking point substantially adapted to the inner-egg borders 17 of the air cell 13. It may be determined, e.g., using transmitted light techniques.

Thus, predetermined breaking points 30 may be created at different points at/in the calcified shell 11 in the region of the air cell 13.

Figure 2:
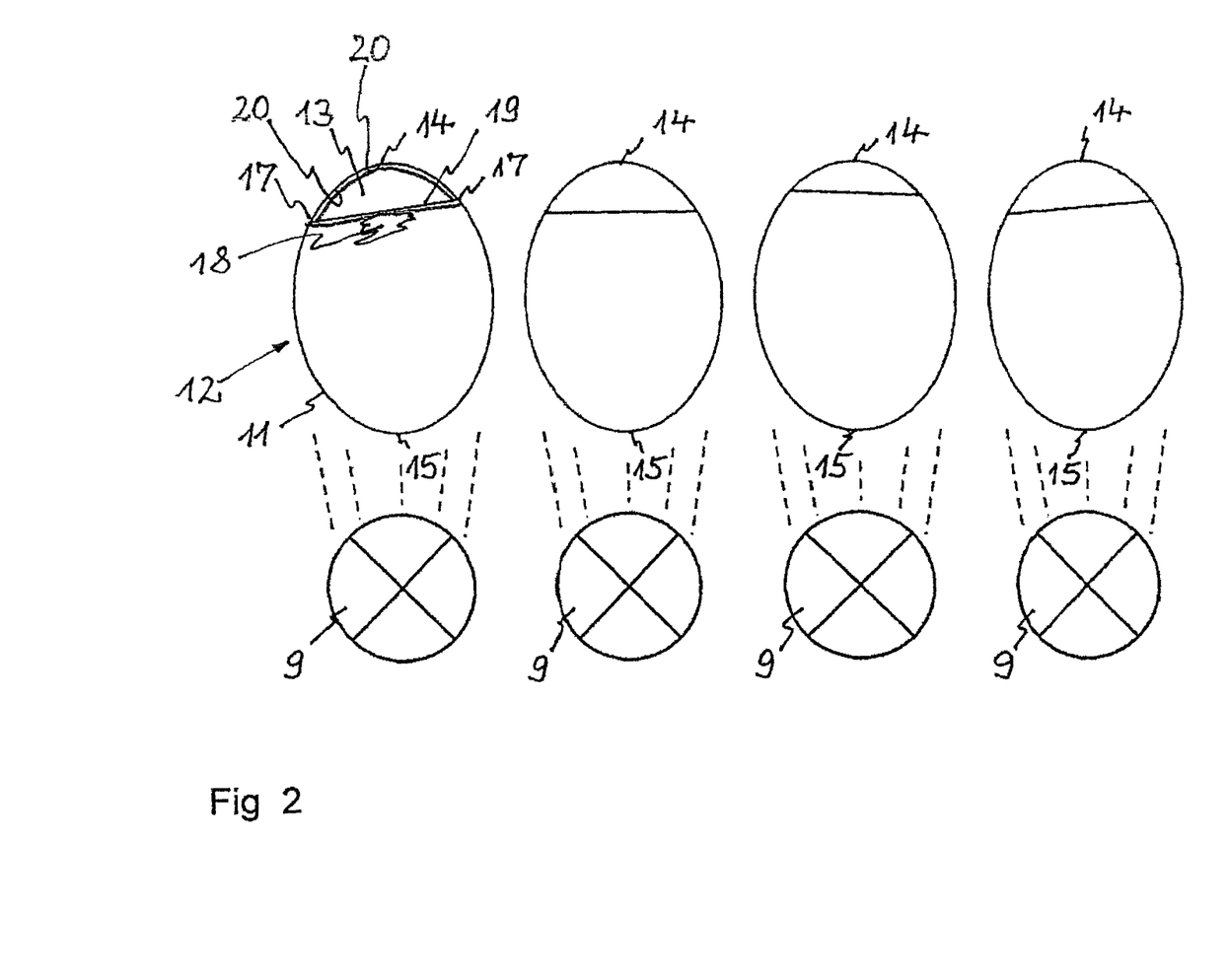
Figure 3:
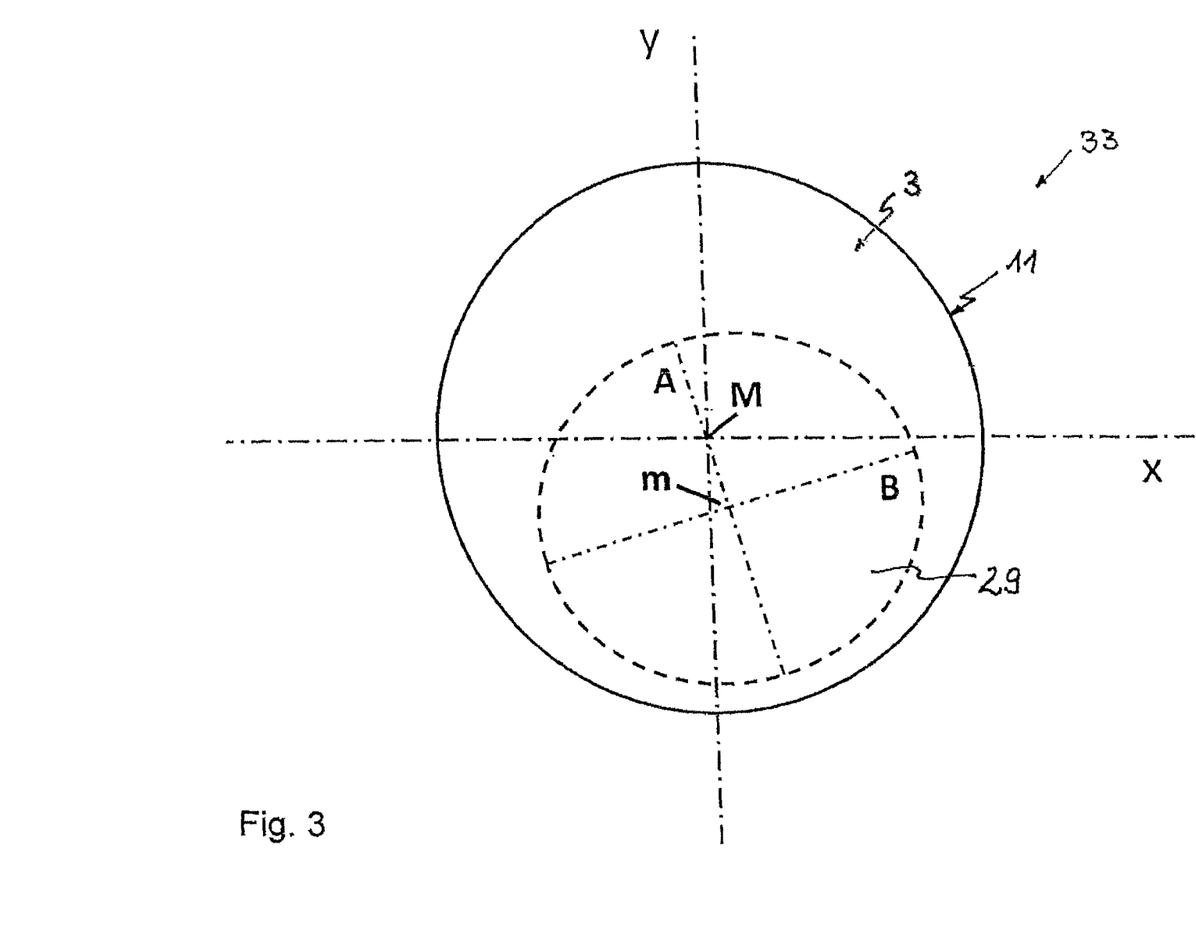

In the following, the method according to the invention for creating an opening 31 in the calcified shell 11 in the region of the blunt end 14 of incubated bird eggs 12 with embryo 18 is described with the help of an exemplary embodiment. According to the method of the present invention, the hatching egg 12 stored with its pointed end 15 facing downwards is dimensioned. The location and the dimensions of the air cell 13 within the region of the blunt end 14 as well as the location of the embryo 18 below the inner membrane shielding the embryo 18 from the air cell 13 are detected. As shown in FIGS. 2 and 3, a two-dimensional projection 3 of the hatching egg 12 with a center M and overlaying therewith a two-dimensional projection 29 of the air cell 13 with a central point m is carried out. The two-dimensional projection 29 of the air cell 13 preferably has an elliptic shape with a point of intersection as a central point m of intersecting major and minor axes A, B of the ellipse. The central point of a circular projection 21 representing the predetermined breaking point 30 is assigned to the point of intersection m of the major and minor axes A, B of the ellipse. The radius R of the circular projection 21 is preferably smaller than half the expansion A/2 of the minor axis A of the ellipse with R<A/2. A calcified shell lid 22 corresponding to the two-dimensional circular projection 21 is lifted and removed from the remaining body of the calcified shell 11. Thus, an opening 31 is achieved in the calcified shell 11 and thus also in the air cell 13.

Prior to the start of dimensioning the hatching eggs 12, the hatching eggs 12 are disinfected preferably at least in the region of the blunt end 14.

The method according to the present invention preferably comprises the following steps: detecting the positions and geometries of the already disinfected hatching eggs 12 stored with their pointed ends 15 facing downwards and resting on a predetermined brooding tray 16, detecting the geometry of the hatching eggs 12, detecting the geometry of the air cell 13 at the blunt end 14 of the hatching egg 12, and detecting and digitalizing the geometry data of the volume of the air cell 13. The method may further comprise the following steps: detecting a two-dimensional outline 29 in the form of an area projected onto a surface from the volume projection of the air cell 13 in the shape of an ellipse, calculating the point of intersection m of the major and minor axes A, B of the ellipse 29 from a digitalized camera image 33, calculating the circular projection 21 and the corresponding predetermined breaking point 30 with respect to the point of intersection m of the ellipse, creating an opening 31 in the calcified shell 11 in the circular projection 21 located centrically to the ellipse 29 via the predetermined breaking point 30 above the taut inner membrane 19 with the help of the working device 8, as well as removing the separated part of the calcified shell 11 as a lid 22 in the defined circular projection 21.

Figure 5:
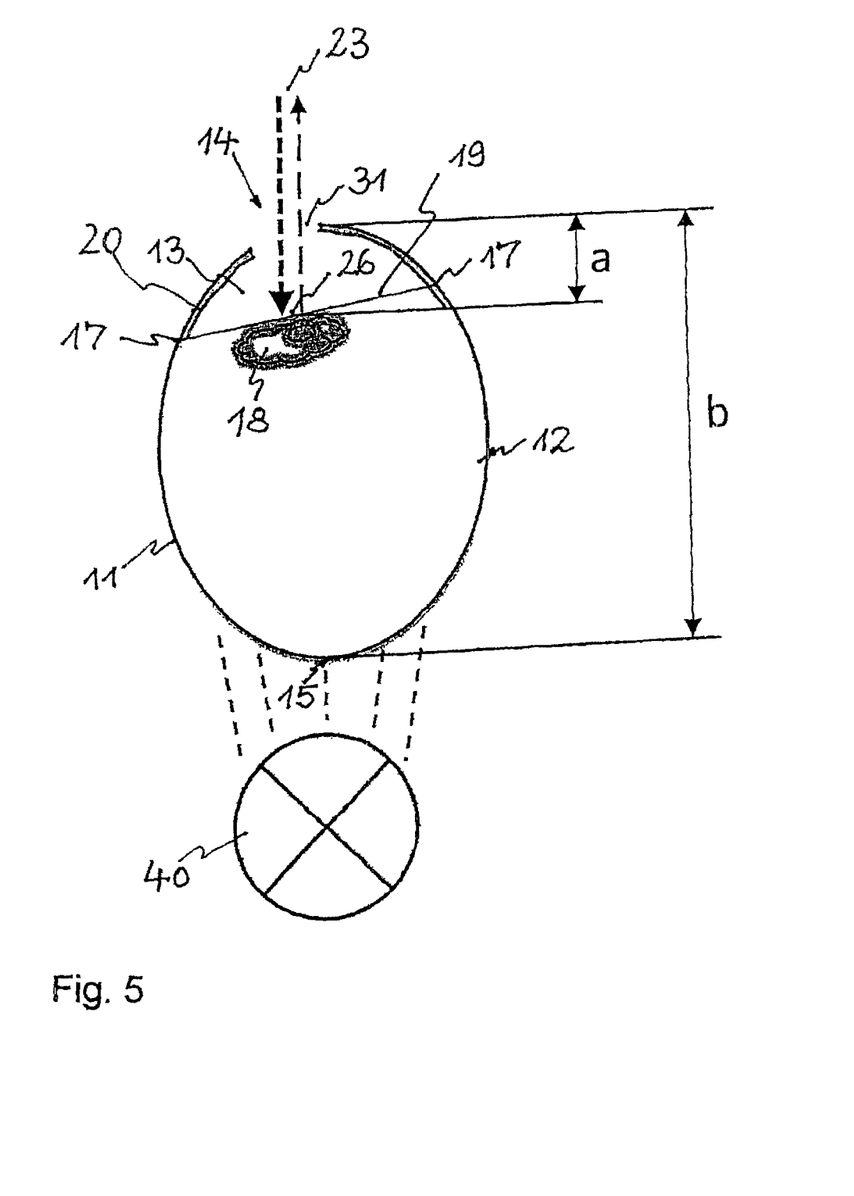

In FIG. 5, the distance a of the inner membrane 19 is calculated starting from the vertex of the egg of the blunt end 14, wherein the detected distance a serves for focusing on the target structure 26 in the region of the inner membrane 19.

After the calcified shell 11 has been opened, the hatching egg 12 is candled again for a second time and an image of the detected region of the inner membrane 19 of the air cell 13 is taken with a color camera 5 for determining the structure 26 for determining the sex, e.g., by means of Raman spectroscopy.

With the help of the color camera 5 and using a light source 40, preferably in the spectral range between 500 nm and 600 nm, an adjusted contrasting of the embryo-specific target structures 26 laying beneath the inner membrane 19 may be set.

With the help of the data received from a distance sensor or a triangulation sensor or a grazing light sensor, wherein the data are assigned to the respective hatching egg 12, the working device 8 is exactly positioned at a position predetermined for the creation of the opening with respect to the calcified shell region 21 of the hatching egg 12 to be worked on.

The enclosure 16 in the form of a tray of the hatching eggs 12 at the transportation device 1 is moved beneath the detection device 2 and the working device 8 for creating the opening 31, wherein by means of the detection device 2a 2D image section 3 or a 3D image section that is converted into a 2D image section is captured of the top view of the hatching egg 12 with the data of said image section being transmitted via electrical connecting lines to the analysis and control unit 6 for further processing, wherein in the analysis and control unit 6 the image data of the 2D image section are processed together with the egg distance data from the distance sensor or the triangulation sensor by means of activated programmatic means, and the processed signals received are forwarded to the working device 8 in order to create the opening 31.

Figure 6:
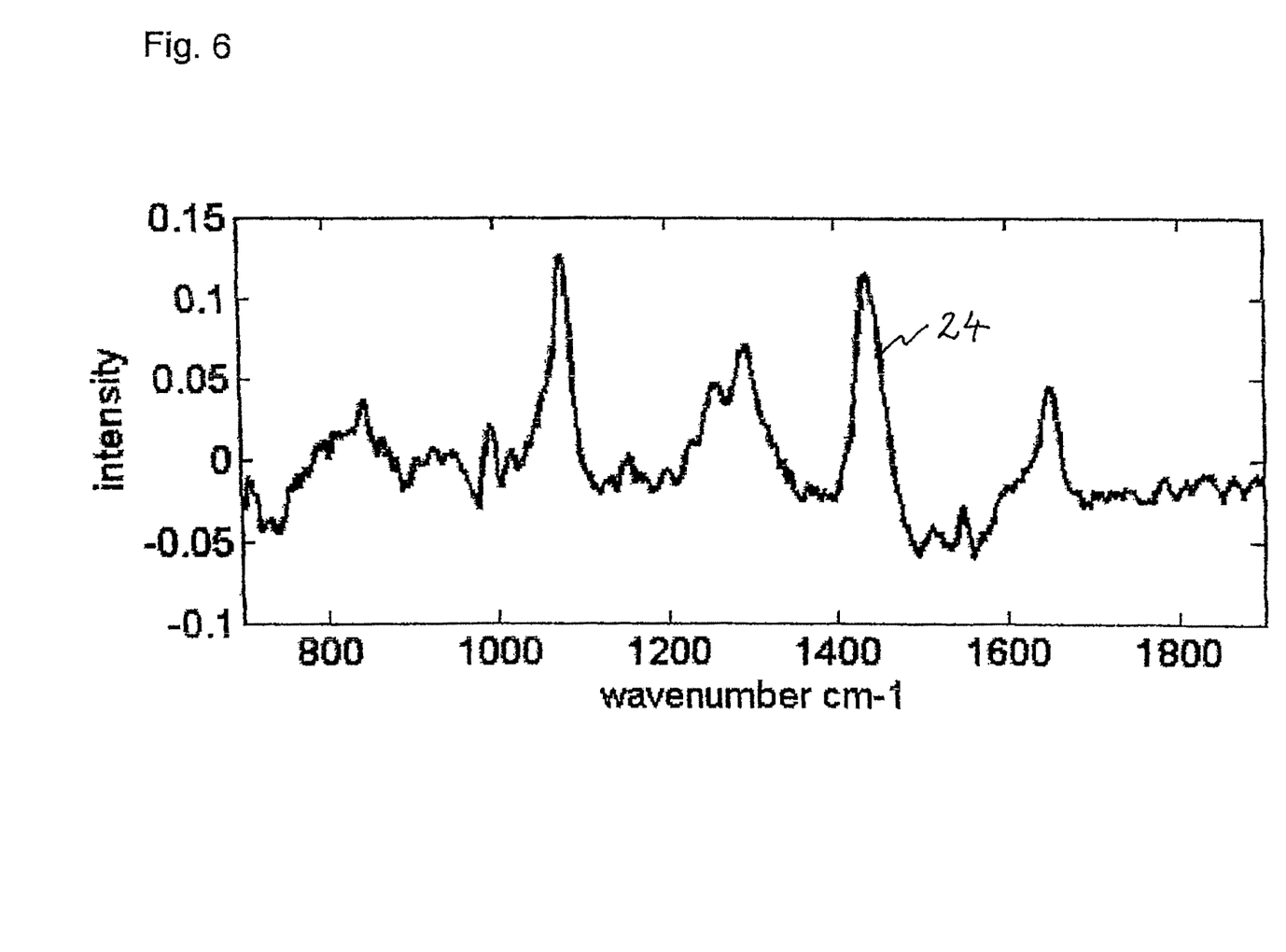

According to FIG. 1, the method for creating an opening 31 in the calcified shell 11 in the region of the blunt end 14 of an incubated bird egg 12 containing an embryo 18 comprises the following steps: conveying the hatching eggs 12 using a conveying device 1a (step 100), disinfecting at least the blunt end 14 (step 110), detecting at least one position area of the conveyed hatching eggs 12 and/or an enclosure 16 containing hatching eggs 12 using a positioning device 35 which is stationed at least in the conveying region of the enclosure 16 containing hatching eggs 12, and converting the respective position area that has been detected into electrical data signals as well as processing the electrical data signals in an analysis and control unit 6 (step 120), candling the hatching egg 12 in order to detect the position of the air cell 13 (step 130), positioning a working device 8 in order to create a predetermined breaking point 30 in the calcified shell 11 of the hatching egg 12 as well as working on the blunt end 14 for creating the opening 31 in the calcified shell 11 of the hatching egg 12 (step 140), removing the lid 22 identified to be located alongside the predetermined breaking point 30 (step 150), focusing the color camera 5 on the target structure 26 to be detected in the region of the inner membrane 19 (step 160), measuring the Raman spectrum 24 of the target structure 26 (embryo) according to FIG. 6 (step 170), closing the opening 31 with a locking element 34 (step 180) and returning the hatching eggs 12 using a returning device 1b in the running direction 25 of the transportation device 1 (step 190).

The step of creating the opening 31 constitutes a defined, target-oriented treatment of the hatching egg 12, wherein the initial positioning by means of the sensor 32 or the sensor array and the final positioning of the hatching egg 12 which is assigned to the creation of the opening and which corresponds to the associated setting position of the working device 8 are carried out using programmatic means saved in the analysis and control unit 6.

In addition to a laser-optical treatment, the aforementioned target-oriented treatment of the calcified shell 11 of the hatching egg 12 may also be carried out by means of mechanical, chemical, or water jet tools.

It may also be advantageous that the treatment can be carried out at incubation temperatures. To this end, the apparatus 10 may, e.g., without the analysis and control unit 6, be incorporated inside a housing (not illustrated) that is adapted to incubating temperatures.

As an input parameter for obtaining the opening 31 in the calcified shell 11 and for detecting the air cell 13 at the blunt end 14, the positions and geometries of the hatching eggs 12 that are typically stored with their pointed ends 15 facing downwards are detected, e.g., by means of laser triangulation or grazing light technologies. The eggs 12 which are, e.g., stored on standard brooding trays 16 are subsequently candled, preferably using white light from below, i.e., starting from the pointed end 15, by means of the first detection device 2 for a first candling step, as is shown in FIG. 2. For this purpose, appropriate light sources 9 (e.g., halogen lamps, LED or standard egg-candlers) are arranged below the brooding tray 16 (FIG. 1 and FIG. 2).

By means of the transmitting light, the geometry of the air cell 13 at the blunt end 14 of the hatching egg 12 is made visible and detected and digitalized with the help of a camera 39 and processed as a 2D image section 3 in the analysis and control unit 6. As indicated in FIG. 2, the geometries of the potential air cells 13 may be of different sizes and be arranged in different inclinations to the longitudinal axis of the respective egg.

In practice, the outline of the area 29 (volume projection of the air cell 13) obtained in this way and projected onto the surface 3, as is shown in FIG. 3, in most cases corresponds to an ellipse.

With the aid of the collected surface data (laser triangulation) and by calculating the point of intersection m of the major and minor axes A, B of the ellipse from the digitalized camera image 33, the predetermined breaking point 30 and thus also the calcified shell lid 22 may then be precisely calculated centrically to the point of intersection m above the taut inner membrane 19, and the calcified shell 11 may thus be opened. For this purpose, lasers for material machining such as, e.g., $CO_2$ lasers are used, but mechanical processes such as milling come into operation as well.

According to FIG. 4, in order to create a sufficiently large opening 31 for subsequent investigations, the calcified shell material is cleared away and removed circularly, partially or in full, preferably with R<A/2 within the predetermined breaking point 30 in the detected region 21 as the calcified shell lid 22. This step may be carried out with the help of either scanning laser optics or a defined movement of rigid laser optics along the desired outline 21 of the predetermined breaking point 30. The lid 22 which is produced in this way may subsequently be removed mechanically, thus creating a free access to the interior of the air cell 13 and to the inner membrane 19 adjoining the interior of the egg.

By way of a repeated use of the laser triangulation or using a simple optical distance meter, the distance a of the inner membrane 19 from the vertex of the egg 14 of the blunt end may be exactly detected at the total height b of the egg 12 according to FIG. 5. For subsequent, e.g., spectroscopic methods, this results in the option of exactly aligning their focus areas with target structures 26 that are to be investigated and that directly adjoin the inner membrane 19, as illustrated in FIG. 5, and of collecting gender-related information. In order to locate the inner target structures 26 (e.g., embryonic blood vessels), the hatching eggs 12 are candled preferably with green light from the light source 40 starting from the pointed end 15, and an image of the exposed region of the inner membrane 19 of the air cell 13 is taken by the color camera 5 and transmitted via signal transfer to the analysis and control unit 6. By way of appropriately adjusting the focus, the analysis and control unit 6 may also serve to detect the distance of the inner membrane 19 with target structures 26 located behind it.

In order to receive an optimized contrasting of the specific target structures 26 (for instance, embryonic blood vessels) that are to be investigated and that are located below the inner membrane 19, the light source 40 may, for example, be used in the green spectral range between 500 and 600 nm for hemoglobin absorption.

With the help of the above-described apparatus 10 and the method according to the present invention, characteristic Raman spectra 24 of embryonic blood vessels 26 may be recorded, e.g., when using IR Raman spectroscopy, as is shown in FIG. 6 for a single Raman spectrum 24, by means of the measuring probe 32 pertaining to the Raman spectra recording unit 38 via the beam path 23 in order to determine the sex of the developing avian embryo 18.

In particular, characteristic Raman spectra 24 may be analyzed with the help of well-known methods of data analysis in order to determine the sex of the developing avian embryo.

For instance, the well-known cluster analysis may be used for analyzing characteristic Raman spectra 24 in order to determine the sex of the developing avian embryo.

The cluster analysis substantially combines two methods, namely principal component analysis (PCA) and k-nearest neighbors classification.

PCA serves for structuring and simplifying the recorded data (e.g., characteristic Raman spectrum according to FIG. 6). In doing so, the measured signal (data, i.e., characteristic Raman spectrum) is depicted by linear combinations in a number that is smaller than that of the measurement values of the signal. This step suppresses the noise during measurement and makes the measured signals more comparable. After the signal has been dissected into its main components, it is possible to set up a mathematical space, i.e., the parameters of each linear combination of a main component correspond to a point in a two-dimensional space in which the axes are any potential combination of the parameters of a potential linear combination. In this way, a point cloud is formed. In the next step, said point cloud is used for k-nearest neighbors classification.

With respect to the signals analyzed here (characteristic Raman spectra), the k-nearest neighbors classification is k=1. This is a special case and is called Voronoi diagram. The obtained point cloud is divided into regions with every point being the center of one region. Different metrics, e.g., the Euclidean distance of the centers to each other, or the size of particular regions may be applied for this construct. Particular combinations of centers and regions are specific for the sex of the developing avian embryo and differ significantly for male and female embryos.

Even if the cluster analysis was exemplarily described here, other data analysis methods may be used for determining the sex of the developing avian embryo on the basis of the recorded signals (data, i.e., characteristic Raman spectra). The aforementioned well-known data analysis methods are also applicable for other analysis methods such as fluorescence spectroscopy or further spectroscopic methods, in particular for the analysis of characteristic spectra.

After the characteristic measurement data have been collected, the opening 31 created in the calcified shell 11 of the blunt end 14 of the hatching egg 12 is mechanically closed again by means of a locking element 34, e.g., by means of a biocompatible plaster (e.g., by means of a medical 3M DuraPore plaster) or a cap. The properties of the locking material that is used are selected so as not to affect the physiology of the hatching egg 12, and particularly so as to avoid an excessive loss of liquid from the air cell 13 by evaporation.

In order to guarantee sterility right from the beginning, a device 27 is provided to disinfect at least the region of the blunt end 14.

While in the exemplary embodiments the methods and the apparatus have been described as an example on the basis of the measured data of Raman spectroscopy, an equivalent utilization is similarly possible with the help of absorption-spectroscopic techniques, particularly fluorescence spectroscopy. In order to avoid a repetition of the above descriptions, reference is made to the above-described exemplary embodiments with respect to the use of absorption-spectroscopic techniques, in particular fluorescence spectroscopy.

While the present invention has been described and shown with respect to its preferred embodiments, it is obvious to the person skilled in the art that different modifications and alterations may be performed to it without departing from the scope of protection of the invention. It is intended in this way that the present invention covers the modifications and alterations of this invention provided that they are covered by the scope of protection of the accompanying patent claims and their equivalents.

Furthermore, different features that are described in connection with the method according to the invention may also form a basis for features of the apparatus according to the invention, and vice versa. Even if specific features have been described in combination with other features, the present invention is not to be limited to these combinations. Rather, an arbitrary combination, as far as it makes technical sense, of the described features is possible.

LIST OF REFERENCE SIGNS

1 transportation device
1a conveying device
1b returning device
2 detection device for detecting the dimensions of the egg
3 2D image section
4 detection device for detecting the dimensions of the air cell
5 color camera focusing on a target structure 26
6 analysis and control unit
7 closing device
8 working device
9 first light source for a first candling step/first candling device
10 apparatus according to the invention
11 calcified shell
12 hatching egg 13 air cell within the egg
14 blunt end
15 pointed end
16 enclosure/brooding tray
17 linking border between air cell and inner membrane
18 embryo
19 inner membrane
20 outer membrane
21 breaking point projection
22 calcified shell lid
23 beam path for recording a Raman spectrum
24 Raman spectrum in the form of an intensity/wavenumber curve
25 running direction of the conveyor belt
26 target structure/measuring region of the inner membrane
27 device for disinfection
28 device for lifting the lid 22
29 air cell projection
30 predetermined breaking point
31 opening in the calcified shell
32 measuring probe
33 digitalized camera image
34 locking element
35 positioning device
36 marker
37 positioning area
38 Raman spectra recording unit/unit for recording measurement data
39 camera for first candling device 9
40 second light source for a second candling step/second candling device
A first minor axis of the ellipse
B second major axis of the ellipse
a distance between measuring point at the inner membrane and vertex of the blunt end of the egg
b height of the egg
x coordinate
y coordinate
M center of the egg projection
m point of intersection of the air cell projection (ellipse)
R radius of the circular projection with R<A/2
100 process step of conveying
110 process step of disinfecting
120 process step of detecting
130 process step of candling
140 process step of opening
150 process step of removing
160 process step of focusing
170 process step of measuring
180 process step of closing
190 process step of returning

The invention claimed is:

1. A method for creating an opening in the calcified shell of an incubated bird egg containing an embryo, in the region of the blunt end of the incubated bird egg, wherein within the region of the blunt end there is an outer membrane and an inner membrane with an air cell located therebetween, characterized in that the method comprises the following steps:
 a) storing the incubated bird egg with its pointed end facing downwards, wherein the embryo adjoins the inner membrane;
 b) candling the incubated bird egg and detecting the light transmitted through the incubated egg for detecting the position and the geometry of the air cell at the blunt end of the incubated bird egg; and
 c) subsequently creating an opening in the calcified shell at the blunt end of the incubated bird egg above the taut inner membrane to the air cell in order to obtain an access to the air cell.

2. The method according to claim 1, wherein the method further comprises a step for detecting the position and geometry of the incubated bird egg stored with its pointed end facing downwards, wherein the incubated bird egg is preferably located on a predetermined brooding tray.

3. The method according to claim 1, wherein the step for detecting the position and geometry of the air cell comprises a step for determining a two-dimensional projection of the air cell with a central point from the detected light transmitted through the incubated bird egg, wherein said two-dimensional projection of the air cell preferably comprises a substantially elliptic shape with the point of intersection of intersecting major and minor axes of the ellipse as a central point.

4. The method according to claim 3, wherein the central point is used as the center for creating the opening, wherein the opening is preferably circular and has a Radius that at the most corresponds to half the minor axis of the ellipse.

5. The method according to claim 1, wherein the creation of the opening comprises a step for creating a predetermined breaking point in the calcified shell and further a step for removing the region of the calcified shell defined by the predetermined breaking point.

6. The method according to claim 1, wherein, after the opening has been created, the method additionally comprises a further step for candling the incubated bird egg, and a step for detecting the light transmitted through the incubated bird egg, wherein preferably light in the spectral range of 500 nm to 600 nm is used.

7. The method according to claim 6, wherein, prior to detecting the light transmitted through the incubated bird egg, the method comprises a step for determining the distance of the inner membrane starting from the vertex of the egg of the blunt end and a step for focusing the light on the inner membrane using the distance.

8. The method according to claim 6, wherein the method further comprises a step for detecting the position of the embryo using the detected light transmitted through the incubated bird egg.

9. The method according to claim 1, wherein the method further comprises a step for determining the sex of the embryo using absorption spectroscopy, preferably using Raman spectroscopy and/or fluorescence spectroscopy.

10. The method according to claim 1, wherein, after the opening has been created, the method further comprises a step for closing the opening, preferably with a semipermeable membrane composed of a biocompatible material, and further preferably a step for disinfecting at least the blunt end of the incubated bird egg.

11. An apparatus for creating an opening in the calcified shell of an incubated bird egg containing an embryo, in the region of the blunt end of the incubated bird egg, wherein within the region of the blunt end there is an outer membrane and an inner membrane with an air cell located therebetween, wherein the apparatus is preferably configured to carry out the method according to claim 1, characterized in that the apparatus comprises:
 a holder configured to store the incubated bird egg with its pointed end facing downwards, wherein the embryo adjoins the inner membrane;
 a first detection device configured to detect the position and geometry of the air cell, wherein the first detection device comprises a first candling device configured to send light through the incubated bird egg, and a first detector configured to record the light transmitted through the incubated bird egg; and an opening device configured to create an opening in the calcified shell at the blunt end of the incubated bird egg above the taut inner membrane to the air cell so as to obtain an access to the air cell; and a second detection device configured to detect the position and geometry of the incubated bird egg stored with its pointed end facing downwards.

12. The apparatus according to claim 11, wherein the first candling device is arranged below the incubated bird egg and the first detector is arranged above the incubated bird egg and opposite the first candling device.

13. The apparatus according to claim 11, wherein the second detection device is a sensor or a sensor array and preferably comprises a distance sensor or a triangulation sensor.

14. The apparatus according to claim 11, wherein the opening device comprises a working device configured to create a predetermined breaking point in the form of the opening, wherein the working device preferably is a laser-optical device configured to perforate the calcified shell with a laser beam, and wherein the opening device preferably comprises a removal device configured to remove the region defined by the predetermined breaking point.

15. The apparatus according to claim 11, wherein the apparatus further comprises a second candling device arranged below the incubated bird egg and configured to send light through the incubated bird egg, wherein preferably light in the spectral range of 500 nm to 600 nm is used, and wherein the apparatus further comprises a second detector arranged above the incubated bird egg and opposite the second candling device, wherein the second detector is configured to record the light transmitted through the incubated bird egg in order to detect the position of the embryo.

16. The apparatus according to claim 11, wherein the apparatus further comprises an absorption spectroscopy unit configured to determine the sex of the embryo, wherein the absorption spectroscopy unit preferably is a Raman spectroscopy unit and/or a fluorescence spectroscopy unit.

17. The apparatus according to claim 11, wherein the apparatus further comprises a closing device for closing the opening, preferably using a semipermeable membrane composed of a biocompatible material.

18. The apparatus according to claim 17, wherein the apparatus comprises a disinfection device for disinfecting at least the blunt end of the incubated bird egg.

* * * * *